United States Patent [19]
Fell

[11] Patent Number: 5,238,217
[45] Date of Patent: Aug. 24, 1993

[54] FLEXIBLE TUBE CLIP

[75] Inventor: Helmut Fell, Ingbert, Fed. Rep. of Germany

[73] Assignee: MEDINORM Aktiengesellschaft medizintechnische Produkte, Quierschied/Saar, Fed. Rep. of Germany

[21] Appl. No.: 809,494

[22] PCT Filed: Jul. 7, 1990

[86] PCT No.: PCT/DE90/00507
§ 371 Date: Jan. 29, 1992
§ 102(e) Date: Jan. 29, 1992

[87] PCT Pub. No.: WO91/00970
PCT Pub. Date: Jan. 24, 1991

[30] Foreign Application Priority Data

Jul. 8, 1989 [DE] Fed. Rep. of Germany ....... 8908336

[51] Int. Cl.$^5$ .............................................. F16K 7/02
[52] U.S. Cl. ......................................... 251/5; 137/907; 604/250
[58] Field of Search ........... 251/5, 9; 137/907, 505.47; 604/250, 320, 323

[56] References Cited

U.S. PATENT DOCUMENTS 3,984,080 10/1976 Varis et al. ............................. 251/5
4,191,204 3/1980 Nehring .
4,718,895 1/1988 Kurtz et al. .
4,903,726 2/1990 Martin et al. ................... 137/907 X
5,076,322 12/1991 Chobri et al. ................... 137/907 X

FOREIGN PATENT DOCUMENTS 2356480 1/1975 Fed. Rep. of Germany .
2444472 12/1978 France .
88/05319 7/1988 World Int. Prop. O. .

OTHER PUBLICATIONS

German Patent Application No. G 86 10 275.3.

Primary Examiner—John C. Fox
Attorney, Agent, or Firm—Collard & Roe

[57] ABSTRACT

A hose clamp (50) for a hose (18), inside which a different pressure prevails from that of its environment, and having two arms (28, 30) between which said hose (18) may be squeezed with different forces and thus the hose cross-section may be closed, is characterized in that the two arms (28, 30) are mutually movable transversely to the longitudinal axis of the hose (18), a bellows-like body (38) is arranged between the two arms (28, 30) in such a way that, by the expansion and compression of said body (38), the arms (28, 30) are movable in relation to each other and thus the hose (18) may be compressed to differing degrees, and the inside of the bellows-like body (38) may be connected to the hose (18) via a subsidiary line (48).

11 Claims, 2 Drawing Sheets

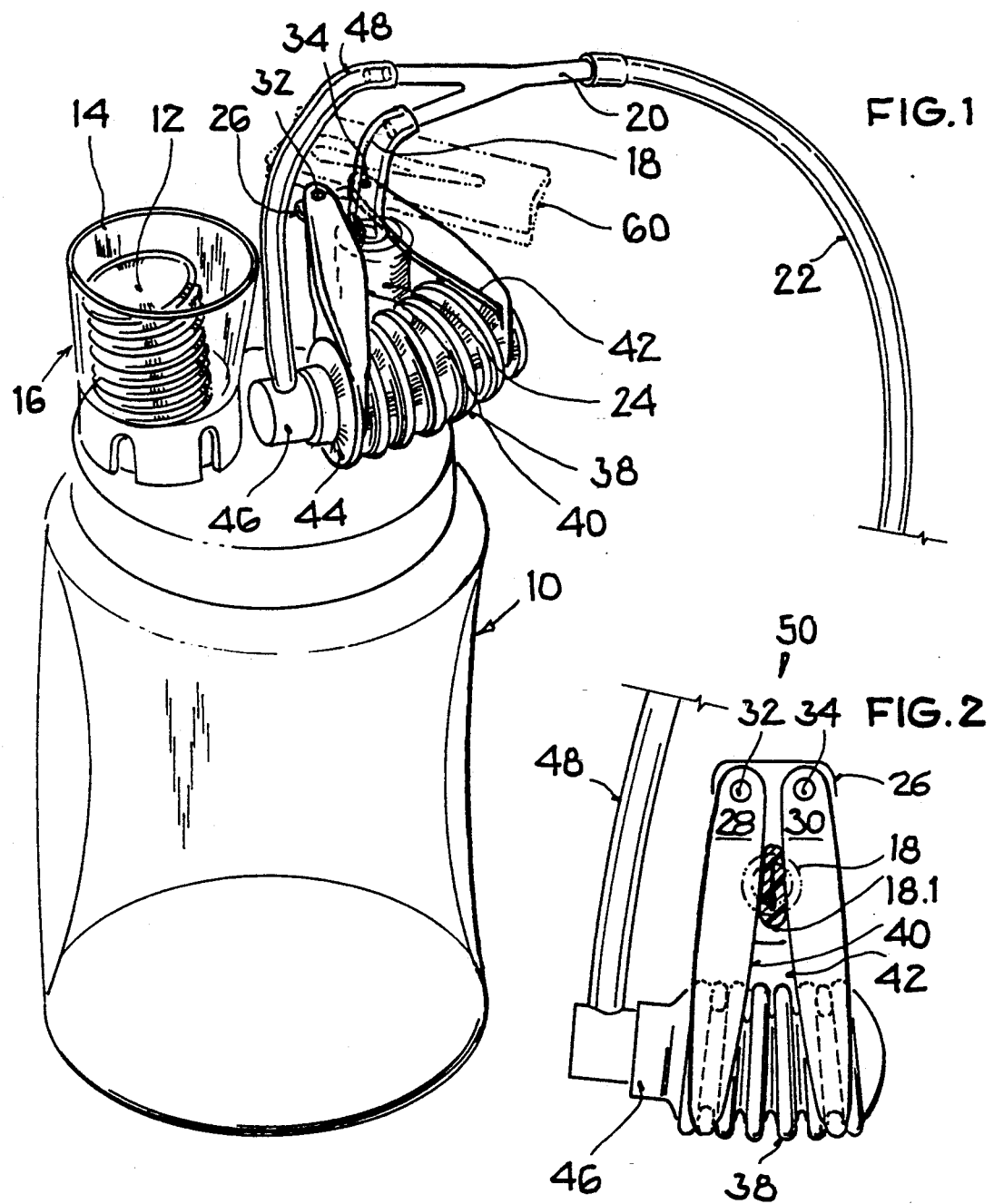

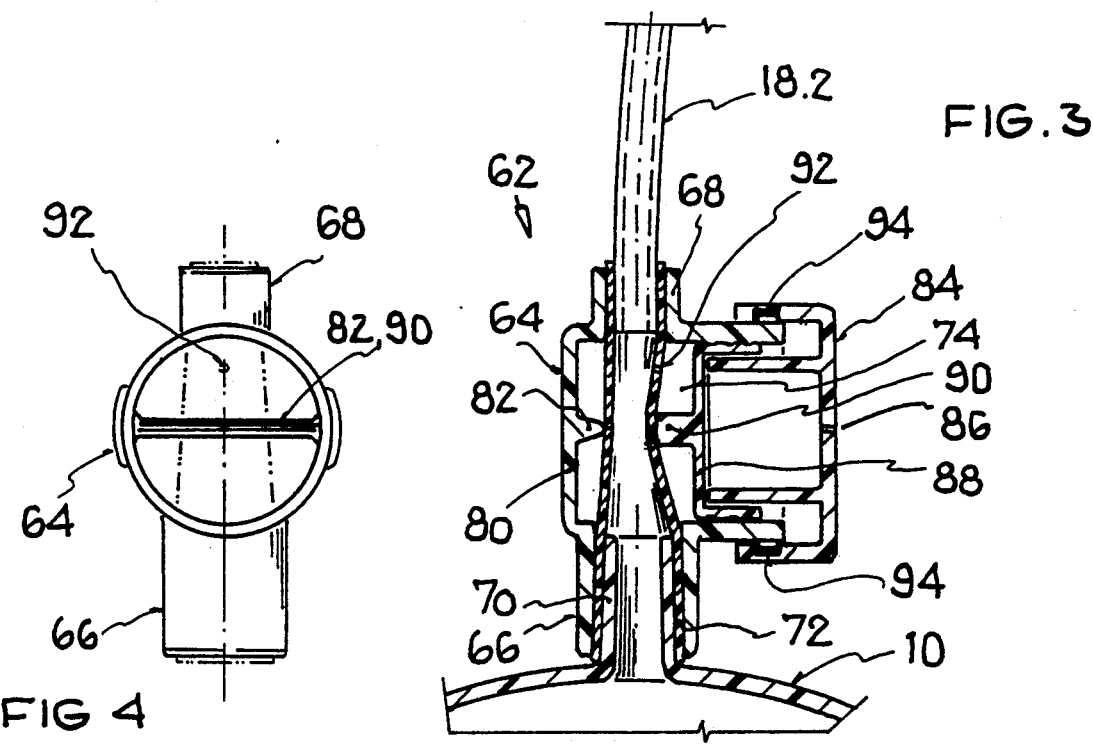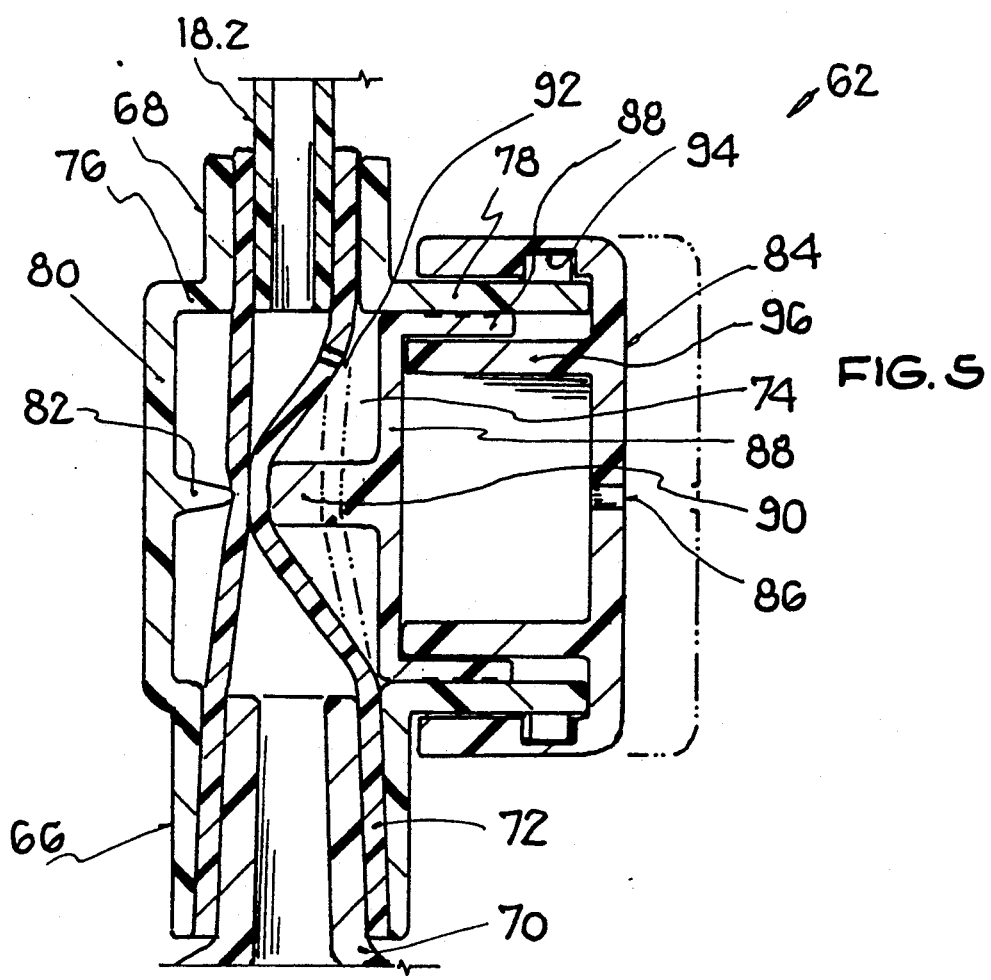

FLEXIBLE TUBE CLIP

TECHNICAL FIELD

The invention relates to a clip for a flexible tube in the interior of which the pressure prevailing is different from that in its environment. Flexible tube clips of this kind are therefore suitable for both sub-and superatmospheric pressure systems. A preferred field of use of a flexible tube clip of this kind is medical technology, in which a clip of this kind can be used as a connection means for a vacuum suction flask for drawing off wound fluids in the drainage of wounds. A suction flask of this kind is connected by means of a flexible tube to a perforated wound drainage tube, which in turn is introduced into a hermetically sealed wound cavity. The negative pressure prevailing in the suction flask thus also acts in the wound cavity, so that wound secretions forming there can be sucked off into the flask.

PRIOR ART

So-called sliding clips are known (DE-A-37 24 483) for closing a flexible tube, such as for example the tube disposed between the vacuum suction flask and the wound drainage tube. These sliding clips have two fork-like prongs which are fastened to one another, widening out in a V-shape. By sliding these prongs lengthwise relative to the tube, the cross-section of the tube can be compressed and the tube thus closed. Sliding clips of this kind permit practically no regulation, that is to say partial closure of the tube cross-section.

Nevertheless, it is often necessary for tubes to be only partially closed. This need arises, for example, in the case of the abovementioned suction flask in medical technology. For reasons of economy a maximum vacuum is desirable in the suction flask in order to enable the greatest possible amount of secretions to be sucked into the flask. On the other hand, this high vacuum also acts through the tube on the wound to which vacuum also acts through the tube on the wound to which the flask is connected. This is less desirable because of the consequent high suction load in the wound region. The resulting conflict of aims is solved by using suction flasks not having a maximum vacuum. In this respect, it must be borne in mind that the suction flask and its tube connections are disposable items, which means that the cost of their manufacture must be as low as possible.

A flexible tube clip of the type defined, with the aid of which the cross-section of a tube can be closed to a greater or lesser extent for regulation purposes, is known from DE-B-23 56 480. The valve of a container disclosed there is provided in its cover region with a lever which rests on both a rubber balloon and a flexible tube. In addition, this lever has a double mounting so that it can turn in both the clockwise direction and the counter-clockwise direction. The interior of the rubber balloon is connected to a pipe projecting into the interior of the container. The flexible tube, on which the lever likewise rests, constitutes an additional connection of the interior of the container to the environment of the container. On the contraction of the rubber balloon, that is to say on a reduction of the volume of its interior space, the lever turns, for example, in the counter-clockwise direction. When the rubber balloon is inflated, that is to say on the enlargement of its interior space, the lever turns in the clockwise direction, that is to say in the opposite direction. In both directions of its turning, the lever reduces the load on the flexible tube, so that the cross-section of the latter is enlarged in both cases. Since the interior of the rubber balloon is in communication with the interior space of the container via the pipe, the pressure in the rubber balloon will become equal to that prevailing in the interior of the container. If the internal pressure of the container falls below a predetermined value, the rubber balloon will contract and free the cross-section of the flexible tube. The pressure inside the container thus rises again to the preset value. If, on the other hand, the internal pressure of the container exceeds the predetermined value, the rubber balloon expands and the cross-section of the flexible tube will likewise open. This has the consequence that the positive pressure in the balloon is reduced and drops back to the preset value. This flexible tube clip thus serves to regulate the internal pressure of the container to a determined value dependent on the outside pressure. When the internal pressure in the container falls below a determined value, this lower pressure which is adjusted is immediately raised again by the opening of the cross-section of the flexible tube. The cross-section of the flexible tube thus does not act as a throttle point. It is thus not possible to ensure that outside the more or less sharply constricted cross-section of the flexible tube a constant negative pressure largely independent of the negative pressure prevailing in the container can be maintained.

SUMMARY OF THE INVENTION

Starting from this prior art, the problem underlying the invention is that of providing a flexible tube clip of the kind indicated in the preamble, which constitutes a simple possible way of reducing the cross-section of a flexible tube in order thereby to form a throttle restriction at that point in the cross-section of the tube.

This invention is indicated by the features of the main claim. Advantageous further developments and elaborations are the subject of the subclaims.

The flexible tube clip according to the invention, for a flexible tube which is connectable to a container and in whose interior the pressure prevailing is different from that in its environment, according to the preamble of Patent Claim 1, is accordingly characterized in that the connection between the interior space of the subsidiary chamber and the flexible tube is a subsidiary tube or an opening provided only outside the container, the subsidiary tube or the opening is connected, in relation to the clamp point, on the side of the flexible tube remote from the container which is to be connected, the arms are disposed on the wall of the subsidiary chamber in such a manner that through variation of the volume of the subsidiary chamber the arms are movable relative to one another and the flexible tube can thereby be compressed to different extents, while the two arms of the body forming the subsidiary chamber move towards one another when the negative pressure in the flexible tube increases, and the two arms of the body forming the subsidiary chamber move away from one another only when the negative pressure in the flexible tube is reduced.

A flexible tube clip of this kind, installed in a tube connection between, for example, a vacuum suction flask and a wound drainage tube, can thus act independently as a throttle valve because the pressure prevailing in the tube also acts through the subsidiary tube in the interior space of the subsidiary chamber and has the effect of correspondingly adjusting the interior space in relation to the prevailing outside pressure. When a negative pressure prevails in the tube, this negative pressure thus also acts in the subsidiary chamber, so that the latter can contract and thus, the at least one arm connected to it can make a relative movement toward the other arm. This in turn has the consequence that the arms will compress the cross-section of the tube to a determined extent. The tube clip will compress the tube to such an extent that equilibrium is achieved between the negative pressure acting through the cross-section of the tube, and the negative pressure in the subsidiary chamber. With the aid of a tube clip of this kind, it is thus possible to use a vacuum flask having a maximum vacuum without this maximum vacuum them also prevailing in, for example, the region of a wound.

In a first advantageous development of this tube clip, the subsidiary chamber is formed by a bellows-like body which is disposed between the two arms in such a manner that through the expansion or contraction of said body the arms are movable relative to one another and thus, the tube is compressed to different extents. In such an arrangement, it is expedient for the two arms to be swivellably fastened to a sleeve member; the sleeve member can in this case be so constructed that it can be pulled over the respective tube which is to be pinched by the clip. In addition, the bellows-like body is fastened by its two end regions to the two arms. The throttle action of a tube clip of this kind depends on the materials and the constructional arrangement relative to one another of the individual components used.

In order to vary this throttle action determined by design, an elastic body acting as damping means can be additionally disposed between the two arms. Depending on where this elastic body is disposed, the throttle action can be strengthened or weakened. According to another embodiment of the invention, this effect can also be achieved through the fact that the bellows-like body can be fastened at various points along the arms. be connected, the arms are disposed on the wall of the subsidiary chamber in such a manner that through variation of the volume of the subsidiary chamber the arms are movable relative to one another and the flexible tube can thereby be compressed to different extents, while the two arms of the body forming the subsidiary chamber move towards one another when the negative pressure in the flexible tube increases, and the two arms of the body forming the subsidiary chamber move away from one another only when the negative pressure in the flexible tube is reduced.

A flexible tube clip of this kind, installed in a tube connection between, for example, a vacuum suction flask and a wound drainage tube, can thus act independently as a throttle valve because the pressure prevailing in the tube also acts through the subsidiary tube in the interior space of the subsidiary chamber and has the effect of correspondingly adjusting said interior space in relation to the prevailing outside pressure. When a negative pressure prevails in the tube, this negative pressure thus also acts in the subsidiary chamber, so that the latter can contract and thus the at least one arm connected to it can make a relative movement towards the other arm. This in turn has the consequence that the arms will compress the cross-section of the tube to a determined extent. The tube clip will compress the tube to such an extent that equilibrium is achieved between the negative pressure acting through the cross-section of the tube and the negative pressure in the subsidiary chamber. With the aid of a tube clip of this kind it is thus possible to use a vacuum flask having a maximum vacuum without this maximum vacuum then also prevailing in, for example, the region of a wound.

In a first advantageous development of this tube clip the subsidiary chamber is formed by a bellows-like body which is disposed between the two arms. In such an arrangement it is expedient for the two arms between which the body is disposed to be swivellably fastened to a sleeve member; the sleeve member can in this case be so constructed that it can be pulled over the respective tube which is to be pinched by the clip. In addition, the bellows-like body is fastened by its two end regions to the two arms. The throttle action of a tube clip of this kind depends on the materials and the constructional arrangement relative to one another of the individual components used.

In order to vary this throttle action determined by design, an elastic body acting as damping means can be additionally disposed between the two arms. Depending on where this elastic body is disposed, the throttle action can be strengthened or weakened. According to another embodiment of the invention this effect can also be achieved through the fact that the bellows-like body can be fastened at various points along the arms.

Instead of the bellows-like body it is also possible to provide a piston and cylinder arrangement, in such a manner that the interior space of the subsidiary chamber is in this case formed by the interior space delimited by the cylinder, the piston and the wall of the tube. In this case at least one of the arms is fastened to the piston in such a manner that on the displacement of the piston in the cylinder said arm is moved transversely to the longitudinal axis of the tube. The other arm, which bears against the tube, can in this case be stationary. The second arm may also be formed by some other construction surrounding the tube, such as for example a wall part.

In a practical way the piston is movable in the direction of the tube against the force of an elastically deformable body. This elastically deformable body may be an elastically resilient spring. It is, however, also possible for the tube to be made elastically resilient, at least in its region which is compressible by the arms. If the tube is completely compressed, and thus its wall undergoes maximum deformation in this compressible region, the restoring fore existing in the tube wall will be directed against the piston force pressing against it, so that on a reduction of the negative pressure in the subsidiary chamber, the restoring force of the tube will push the piston away from the tube wall and therefore back.

Other advantages of the invention can be seen in the further features indicated in the subclaims.

BRIEF DESCRIPTION OF THE DRAWING

The invention is described and explained more fully below with the aid of the examples of embodiment illustrated in the drawing, in which:

FIG. 1 is a view in perspective of a vacuum flask with an attached connecting flexible tube to which a first embodiment of the tube clip according to the invention is fastened, FIG. 2 is a plan view of the tube clip shown in FIG. 1, mounted on the connecting tube, FIG. 3 is a side view of a second embodiment of a tube clip according to the invention, mounted on a vacuum flask, in its throttle position, FIG. 4 is a side view of the tube clip shown in FIG. 3, partly in section, and FIG. 5 is a longitudinal section through the tube clip according to the invention shown in FIG. 3, with the suction flask in the closed state.

WAYS OF EMBODYING THE INVENTION

On a first opening of a vacuum suction flask 10 is disposed a bellows 12 of plastics material, which is surrounded by a transparent, approximately cylindrical protective cup 14 (FIGS. 1 and 2). The bellows 12 and the protective cup 14 serve as a pressure indicator 16 for the negative pressure prevailing in the interior of the suction flask 10. A bellows 12 at maximum expansion indicates a minimum negative pressure in the suction flask 10, and an extremely highly contracted bellows 12 indicates a maximum negative pressure therein.

A tube 18 is connected to a second opening of the suction flask 10. This tube 18 is connected via a tube fork 20 to a tube 22 which can be connected to a drainage tube (not shown).

A connection piece 24 is engaged over the tube 18. At its end directed away from the suction flask 10 this connection piece 24 is provided with a collar piece 26. Two arms 28, 30 are swivellably fastened by their ends, with the aid of respective joints 32 and 34, to said collar piece 26.

The other ends of the two arms 28, 30 are fastened to a bellows 38. On the contraction of this bellows 38 the mutually facing inner sides 40, 42 of the two arms 28, 30 are moved towards one another and to a greater or lesser extent compress the cross-section of the tube 18 lying between them.

At that end face 44 of the bellows 38 which lies on the left in the drawing, one end of a tube 48 is connected with the aid of a connection piece 46. The other end of said tube 48 is connected to the still free end of the tube fork 20. The tube 18 and the tube 22 are fastened to the other two ends of said tube fork 20. The tube clip 50 mounted on the tube 18 operates in the following manner:

When the tube clip 50 is in the open state, as shown in FIG. 1, the same negative pressure prevails in the tube 22 as in the vacuum suction flask 10. This same negative pressure acts for only a very short time, because this negative pressure is also formed, through the tube 48, in the bellows 38. Through this negative pressure, however, the bellows 38 will contract, so that the arms 28, 30 connected to it will draw together, as shown for example in FIG. 2. The relatively soft tube lying between the arms 28, 30 is therefore compressed from its open position 18 shown in dot-dash lines, so that it assumes the compressed position 18.1 shown in solid lines in FIG. 2. On those sides of the arms 28, 30 which are directed away from the suction flask 10 a negative pressure reduced relative to the interior of the suction flask 10 therefore prevails. This reduced negative pressure thus also acts in the tube 22 and consequently also in the wound drainage tube which, for example, is connected to the latter. Despite maximum negative pressure in the vacuum suction flask 10, only a reduced negative pressure therefore acts in a, for example, human wound from which wound secretions are to be sucked off into the vacuum suction flask 10.

In order to maintain the maximum negative pressure in the vacuum suction flask 10 before the latter is used, a sliding clip 60, shown in dot-dash lines, is pushed on the tube 18 in such a manner that the latter is completely closed at that point. The bellows 38 is thus connected to the atmosphere existing outside the bellows 38, so that it is at maximum expansion. The bellows 38, which for reasons of economy is made of plastics material, is therefore in the relaxed state. Its elastic deformability is thus not impaired; this could not otherwise be ensured if it were kept compressed for a long time because of the risk of fatigue of the plastics material of which it is made. As soon as the suction flask 10 is connected for its intended purpose to, for example, a human wound, the sliding clip 60 is removed from the tube 18. The bellows 38 will thus abruptly contract and compress the tube 18 to a predetermined extent, as illustrated by way of example in FIG. 2.

The tube clip 62 according to the invention which is illustrated in FIG. 3 comprises a casing 64 provided with a bottom connection piece 66 and a top connection piece 68. The bottom connection piece 66 is fitted gastightly on the neck 70 of the vacuum flask 10. A transition tubing piece 72 is fitted, likewise gastightly, between the connection piece 66 and the neck 70. This tubing piece 72 passes through the interior space 74 of the casing 64 and projects out of the casing 64 in the region of the top connection piece 68. A flexible tube 18.2 is gastightly connected in the region of the top connection piece 68. The interior of the tube 18.2 is thus connected to the interior of the vacuum flask 10.

On the two sides of the transition tubing piece 72 the casing 64 has a left-hand flange 76 and an oppositely disposed right-hand flange 78. A wall 80 adjoins the left-hand flange 76. This wall has a central cantilever projection in the form of a left-hand arm 82. The wall 80 and therefore also the casing 64 are in contact with the transition tubing piece 72 only in the region of said left-hand arm 82, that is on the left in the drawing.

On the side of the casing 64 opposite the wall 80 the flange 78 disposed there is covered by a cap-like cover 84. An opening 86 is formed in this cover 84, so that the atmospheric pressure prevailing outside the cover 84 also acts inside the latter.

A piston 88 is guided in the flange 78 for longitudinal sliding, towards the left and the right in the example illustrated. The piston 88 bears gastightly against the inside of the flange 78. In the present case this piston 88 is made of rubber. Said piston 88 has a cantilever projection in the form of a right-hand arm 90, which in relation to the transition tubing piece 72 is disposed exactly opposite the left-hand arm 82. When the piston 88 has been displaced entirely to the left, the transition tubing piece 72 is compressed to an extremely great extent in the region between the left-hand arm 82 and the right-hand arm 90. This condition is illustrated in FIG. 5.

An opening 92 is provided in the wall of the transition tubing piece 72 in the region of the casing 64. The pressure in the interior space of the transition tubing piece 72 can thus come into equilibrium with the pressure prevailing in the casing 64 between the wall 80 and the piston 88.

The cover 84 and the flange 78 are provided with an interlocking device 94, for example of the bayonet type, so that the cover 84 can be fastened in its position shown in FIG. 5. IN this position of the cover 84 the latter, by means of all parts 96 formed on it, presses the piston 88 extremely far to the left, so that the transition tubing piece 72 is completely compressed. The pressure prevailing in the vacuum flask is thus retained in the latter. The position of the tube clip 62 shown in FIG. 5 is that before the suction flask 10 is used. In this position, the vacuum flask 10, with the tube clip 62 attached to it, is taken to a patient.

After the tube 18.2, or the drainage tube connected to it at its end, has been inserted gastightly into a patient's wound, the cover 84 is unlocked, that is to say the bayonet-type locking device 94 is unlocked. The cover 84 will then occupy approximately the position shown in FIG. 3, which means that the passage through the transition tubing piece 72 is opened to a greater or lesser extent. The negative pressure prevailing in the vacuum flask 10 will then be propagated through the tube 18.2 into the region of the patient's wound.

In the region between the arms 82 and 90 a throttle point is thus likewise formed. This throttle point is influenced by the position of the piston 88. The outside pressure prevailing outside the casing 94, for example atmospheric pressure, which can also establish itself in the interior space 74 of the cover 84 by way of the opening 96, acts on said piston 88 from the direction of the cover 84. On the other side of the piston 88, the suction pressure which results from the negative pressure in the vacuum flask, and is normally lower than the outside atmospheric pressure, will act. By virtue of the presence of the opening 92 this pressure can also establish itself on the side of the piston 88 which is on the left-hand side in the drawing, in the interior space 74. As soon as the pressure prevailing in the interior space 74 is, for example, increased, although in absolute terms still remaining lower than the prevailing outside pressure, the piston 88 is moved to the right because of the elastic construction of the transition tubing piece 72, that is to say because of its restoring force. In dependence on the prevailing outside pressure, the pressure in the vacuum flask, and the elastic restoring force of the transition tubing piece 72, a more or less sharply defined throttle point will thus be formed between the arms 82 and 90 inside the casing 64.

Like the tube clip 50, the tube clip 62 thus also provides a very simple possible way of self-regulating formation of a throttle point in a flexible tube.

I claim:

1. A flexible tube clip for a flexible tube having an interior which can be connected to a container and in said interior the pressure prevailing is different from that in its environment, comprising:
   two arms between which the flexible tube is compressible to different extents so that the tube cross-section is closable, said tube having a longitudinal axis;
   the two arms being movable relative to one another transversely to the longitudinal axis of the flexible tube;
   a subsidiary chamber body having an interior space and having an outer wall, the interior space of which has a connection to the flexible tube;
   said outer wall being at least partly resilient so that the volume of the interior space is variable, with one variation of the volume the two arms are movable relative to one another and thus the flexible tube is compressible to different extents;
   the connection means between the interior space of the subsidiary chamber and the flexible tube comprising a subsidiary tube, or an opening in the flexible tube, which subsidiary tube or opening is disposed only outside said container;
   said subsidiary tube or said opening is connected, in relation to a clamp point, on the side of the flexible tube remote from the container which is to be connected;
   said arms being disposed on the wall of the subsidiary chamber in such a manner that through variation of the volume of the subsidiary chamber, the arms are movable relative to one another and the flexible tube can thereby be compressed to different extents;
   wherein the two arms move toward one another when the negative pressure in the flexible tube increases; and
   wherein the two arms move away from one another only when the negative pressure in the flexible tube is reduced.

2. The flexible tube clip according to claim 1, wherein the subsidiary chamber comprises a bellows-like body which is disposed between said two arms.

3. The flexible tube clip according to claim 2, further comprising
   a sleeve member;
   means for swivellably fastening said two arms to said sleeve member;
   said sleeve member positioned over the flexible tube; and
   the bellows-like body being fastened by its two end regions to the two arms.

4. The flexible tube clip according to claim 2, wherein said two arms are connected together by at least one elastic body.

5. The flexible tube clip according to claim 2, wherein said bellows-like body is fastened on the two arms in such a manner as to be adjustable along the arms.

6. The flexible tube clip according to claim 2, wherein said flexible tube clip is made of plastic material.

7. The flexible tube clip according to claim 1, further comprising
   a cylinder having a piston, the cylinder closed at one end face and at that point the flexible tube passes therethrough;
   the flexible tube being gastightly fastened to the cylinder;
   the cylinder connected via an opening in a transition tube piece to the interior space of the cylinder, and the other end face of the cylinder closed by the piston gastightly movable in the cylinder;
   the cross-section of the opening is smaller than the cross-section of the flexible tube at the point at which the opening is situated in the flexible tube;
   the interior space of the subsidiary chamber is formed by the interior space surrounded by the cylinder, the piston and the transition tube wall; and
   at least one of the arms is fastened to that wall of the piston which faces the interior space in such a manner that on the displacement of the piston said arm is movable transversely to the longitudinal axis of the tube and the tube is thereby compressible to different extents.

8. The flexible tube clip according to claim 7, wherein said piston can be moved toward the flexible tube against the force of an elastically deformable body.

9. The flexible tube clip according to claim 8, wherein at least that region of the flexible tube which is situated in the region of the two arms is capable of elastically resilient deformation.

10. The flexible tube clip according to claim 9, wherein
    the region of the flexible tube between the two arms is formed by said transition tube piece capable of elastically resiliently deformation;
    at one end of said tube piece, the flexible tube is connected; and
    at the other end of this tube piece, the container is connected, gastightly in each case.

11. The flexible tube according to claim 8, wherein the elastically resilient body is a spring.

* * * * *